United States Patent
Kim et al.

(10) Patent No.: US 7,291,429 B2
(45) Date of Patent: Nov. 6, 2007

(54) NAPHTHALENETETRACARBOXYLIC ACID DIIMIDE DERIVATIVES AND ELECTROPHOTOGRAPHIC PHOTOCONDUCTIVE MATERIAL USING THE DERIVATIVES

(75) Inventors: Beom-jun Kim, Seongnam-si (KR); Saburo Yokota, Suwon-si (KR); Kyung-yol Yon, Seongnam-si (KR); Hwan-koo Lee, Suwon-si (KR); Seung-ju Kim, Suwon-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 203 days.

(21) Appl. No.: 10/859,318

(22) Filed: Jun. 3, 2004

(65) Prior Publication Data

US 2005/0112482 A1    May 26, 2005

(30) Foreign Application Priority Data

Nov. 21, 2003    (KR) .................. 10-2003-0083035

(51) Int. Cl.
   *G03G 5/06*    (2006.01)
(52) U.S. Cl. .................. 430/58.5; 430/78; 546/75
(58) Field of Classification Search .................. 430/78, 430/58.5; 546/75
   See application file for complete search history.

(56) References Cited

U.S. PATENT DOCUMENTS 5,055,367 A    10/1991    Law
6,391,505 B1 *  5/2002    Hamasaki et al. ......... 430/59.4

FOREIGN PATENT DOCUMENTS

| EP | 1 340 755 | 9/2003 |
|----|-----------|--------|
| JP | 58-173748 | 10/1983 |
| JP | 2000-113504 | 4/2000 |
| WO | WO 02/40479 | 5/2002 |
| WO | WO 03095453 A1 * | 11/2003 |

* cited by examiner

Primary Examiner—Christopher RoDee
(74) Attorney, Agent, or Firm—Roylance, Abrams, Berdo & Goodman, L.L.P.

(57) ABSTRACT

Naphthalenetetracarboxylic acid diimide derivatives and an electrophotographic photoconductive material containing the naphthalenetetracarboxylic acid diimide derivatives. The naphthalenetetracarboxylic acid diimide derivatives have a structure represented by the following formula:

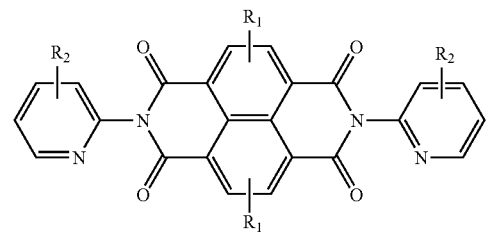

in which, $R_1$ and $R_2$ are each independently selected from the group consisting of a substituted or non-substituted $C_1$-$C_{20}$ alkyl group; a substituted or non-substituted $C_1$-$C_{20}$ alkoxy group; a substituted or non-substituted $C_6$-$C_{30}$ aryl group; and a substituted or non-substituted $C_7$-$C_{30}$ aralkyl group; and halogen. The electrophotographic photoconductive material includes the naphthalenetetracarboxylic acid diimide derivatives as an electron transferring material.

13 Claims, 3 Drawing Sheets

NAPHTHALENETETRACARBOXYLIC ACID DIIMIDE DERIVATIVES AND ELECTROPHOTOGRAPHIC PHOTOCONDUCTIVE MATERIAL USING THE DERIVATIVES

CROSS-REFERENCE TO RELATED APPLICATIONS

This application claims the benefit of Korean Patent Application No. 2003-83035, filed Nov. 21, 2003 in the Korean Intellectual Property Office, the disclosure of which is incorporated herein by reference in its entirety.

BACKGROUND OF THE INVENTION

1. Field of the Invention

The present invention relates to naphthalenetetracarboxylic acid diimide derivatives and an electrophotographic photoconductive material using the same. More particularly, the present invention relates to naphthalenetetracarboxylic acid diimide derivatives that include a specific substituent and have improved electron transporting ability. The invention also relates to electrophotographic photoconductive materials having electrical properties where the electrophotographic photoconductive material uses naphthalenetetracarboxylic acid diimide derivatives as an electron transferring material.

2. Description of the Related Art

The electrophotographic photoconductive material is used for electrophotographic image forming apparatuses including, for example, facsimiles, copying machines, laser printers, cathode ray tube (CRT) printers, light emitting diode (LED) printers, liquid crystal printers, and laser electrophotography. According to the basic working principle of the electrophotographic image forming apparatus, a photoconductive material is electrically charged and exposed to an image-forming light source to form an electrostatic latent image. Next, the latent image is developed using a toner by applying a development voltage. The developed toner image is transferred to a recording medium, followed by fixation of the transferred image.

The electrophotographic photoconductive material has an electrically conductive substrate, and a photoconductive layer that includes a charge generating material, a charge transferring material, a binder resin and other selective additives, where each of the materials are laminated on the electrically conductive substrate. The organic photoconductive layer is largely classified into a single-layer structure having a charge generating material (CGM) and a charge transferring material (CTM) dispersed in a single layer and a multi-layer structure having a CGM and a CTM, which are separately dispersed in a charge generating layer and a charge transferring layer, respectively. The single-layer structure of the photoconductive material is mainly studied for preparation of (+) type organic photoconductive materials while the multi-layer structure photoconductive material is mainly studied for preparation of (−) type organic photoconductive materials.

The (+) type single-layer organic photoconductive material generates less ozone that is harmful to humans and can be produced at a relatively low production cost since it has a single-layer structure.

The photoconductive layer of the (+) type organic photoconductive material includes an electron transferring material, a binder resin, and a charge generating material and may further include a hole transferring material. Since the electron transferring ability of the general electron transferring materials presently used is 100 times less than the hole transferring ability of the hole transferring material, the performance of the organic photoconductive material is largely affected by the electron transferring ability of the electron transferring material. Therefore, among the components contained in the photoconductive layer of the (+) type organic photoconductive material, the electron transferring material is the most important.

The electron transferring ability of the electron transferring material is affected by the solubility of the electron transferring material in an organic solvent and the compatibility to a polymeric binder resin. Therefore, the electron transferring material is selected by considering an organic solvent and a polymeric binder resin used in the photoconductive layer.

Examples of compounds commonly used as the electron transferring material include dicyano fluorenone, 2-nitro-9-fluorenone, 2,7-dinitro-9-fluorenone, 2,4,7-trinitro-9-fluorenone, 2,4,5,7-tetranitro-9-fluorenone, 2-nitrobenzothiopene, 2,4,8-trinitrothioxanthrone, dinitroanthracene, dinitroacridine, dinitroanthraquinone, naphthoquinone, and 3,5-dimethyl-3',5'-di-t-butyldiphenoquinone.

Since compounds having the dicyanofluorenone and diphenoquinone structures exhibit a weak electron transferring ability, an organic photoconductive material including an electron transferring material produced from these compounds may have a reduced charged potential and the exposure potential may increase upon use for a long period of time.

Compounds having a naphthalenetetracarboxylic acid diimide structure provide excellent electron transferring ability since they are much more soluble in organic solvents than compounds having a naphthoquinone structure. However, naphthalenetetracarboxylic acid diimide derivatives which have been developed so far are not sufficiently soluble in organic solvents and are not compatible with polymeric resins. Thus, there is a need for improvement of the electron transferring ability of the compounds.

U.S. Pat. No. 5,468,583 discloses a photoconductive material including a conductive layer, a charge generating layer, and a polymer binder layer having the electron transferring material dispersed therein, in which the electron transferring material has at least one cyclic bisdicarboxylic acid diimide compound represented by the following Formula 1:

[Formula 1]

In the Formula 1, $Q_1$ and $Q_2$ are respectively selected from a branched alkyl group, a non-substituted straight chain alkyl group, a substituted cycloalkyl group, an alkyl-substituted cycloalkyl group, a non-substituted straight-chain unsaturated alkyl group, or hydrogen atom, provided that both $Q_1$ and $Q_2$ are not hydrogen.

$R_1$, $R_2$, $R_3$ and $R_4$, respectively, are each a hydrogen atom, a $C_1$ to $C_4$ alkyl group, a $C_1$ to $C_4$ alkoxy group or a halogen atom.

The electron transferring materials disclosed in the above patent include naphthalenetetracarboxylic acid diimide derivatives as the electron transferring material. However, the naphthalenetetracarboxylic acid diimide derivatives are not sufficiently satisfactory in terms of the solubility in an organic solvent and are not compatible with the binder resin. Also, since they are apt to crystallize and form precipitates in the photoconductive layer and the electron transferring layer, electrophotographic properties of the photoconductive material may be deteriorated.

When naphthalenetetracarboxylic acid diimide derivative compounds are used in a concentration which can maintain compatibility with a binder resin, the photoconductivity of the photoconductive material may be deteriorated.

Japanese Laid-Open Patent Publication No. 2000-113504 discloses an optical recording medium including a naphthalene compound of the following formula:

[Formula 2]

In the Formula 2, A and B are independently an aromatic hydrocarbon group or a polycyclo group which may be substituted. The naphthalene compound disclosed in the above patent is used in an optical recording medium capable of recording and reading since it can be chemically modified by a laser having a wave length of 400 nm to 500 nm. Thus, the naphthalene compounds of the above patent are different from those for an electrophotographic photoconductive material.

Accordingly, there is still a need for the electron transferring material that can provide excellent electron transferring ability through improved solubility in organic solvents and compatibility with polymeric resins.

SUMMARY OF THE INVENTION

The present invention is directed to solving the above problems. Thus, an aspect of the present invention is to provide new naphthalenetetracarboxylic acid diimide derivative compounds with improved electron transferring ability.

Another aspect of the present invention is to provide an electrophotographic photoconductive material using new naphthalenetetracarboxylic acid diimide derivative compounds with improved electron transferring ability.

In order to achieve the above aspects, the naphthalenetetracarboxylic acid diimide derivatives according to an embodiment of the present invention are represented by the following Formula 3:

[Formula 3]

In the Formula 3, $R_1$ and $R_2$ are each independently selected from the group consisting of a substituted or non-substituted $C_1$-$C_{20}$ alkyl group, a substituted or non-substituted $C_1$-$C_{20}$ alkoxy group, a substituted or non-substituted $C_6$-$C_{30}$ aryl group, and a substituted or non-substituted $C_7$-$C_{30}$ aralkyl group, and halogen.

The substituted alkyl group, the substituted alkoxy group, and the substituted aralkyl group may be independently substituted with a substituent selected from the group consisting of an alkyl group, an aryl group, a halogen atom and an alkoxy group.

The substituted aryl group may be substituted with a substituent selected from the group consisting of an alkyl group, an alkoxy group, a nitro group, and a halogen atom.

The electrophotographic photoconductive material according to the embodiment of the present invention has a substrate and a photoconductive layer formed on the substrate, where the photoconductive layer includes a charge generating material and a naphthalenetetracarboxylic acid diimide derivative as the electron transferring material, which is represented by the following Formula 4:

[Formula 4]

In the Formula 4, $R_1$ and $R_2$ are each independently selected from the group consisting of a substituted or non-substituted $C_1$-$C_{20}$ alkyl group, a substituted or non-substituted $C_1$-$C_{20}$ alkoxy group, a substituted or non-substituted $C_6$-$C_{30}$ aryl group, and a substituted or non-substituted $C_7$-$C_{30}$ aralkyl group, and halogen.

The substituted alkyl group, the substituted alkoxy group, and the substituted aralkyl group may be independently substituted with a substituent selected from the group consisting of an alkyl group, an aryl group, a halogen atom, and an alkoxy group.

The substituted aryl group may be substituted with a substituent selected from the group consisting of an alkyl group, an alkoxy group, a nitro group and a halogen atom.

Preferably, the electrophotographic photoconductive material contains the electron transferring material of the above Formula 4 in a ratio of 20 wt % to 40 wt % based on the total solid components.

Preferably, the electrophotographic photoconductive material further includes a hole transferring material.

The photoconductive layer of the electrophotographic photoconductive material may be a single-layer having the charge generating material and the naphthalenetetracarboxylic acid diimide derivative dispersed in a single layer or a laminated, multi-layer structure having the charge generating material and the naphthalenetetracarboxylic acid diimide derivative which are separately dispersed in different layers.

Preferably, the electrophotographic photoconductive material may further include the electron acceptor.

BRIEF DESCRIPTION OF THE DRAWING FIGURES

The above aspects and features of the present invention will be more apparent by describing certain embodiments of the present invention with reference to the accompanying drawing figures, in which.

DETAILED DESCRIPTION OF THE EXEMPLARY EMBODIMENT

The present invention will be explained in detail with reference to the attached drawing figures and Examples.

The naphthalenetetracarboxylic acid diimide derivatives according to an embodiment of the present invention include a pyridine structure. The synthesis of the derivatives is disclosed in the Examples.

The naphthalenetetracarboxylic acid diimide derivatives are represented by the Formula 3, in which, $R_1$ and $R_2$ are each independently selected from the group consisting of a substituted or non-substituted $C_1$-$C_{20}$ alkyl group, a substituted or non-substituted $C_1$-$C_{20}$ alkoxy group, a substituted or non-substituted $C_6$-$C_{30}$ aryl group, a substituted or non-substituted $C_7$-$C_{30}$ aralkyl group, and halogen.

If $R_1$ or $R_2$ is an alkyl group, the alkyl group may be a $C_1$-$C_{20}$ straight or branched alkyl group. Since respective molecules of the naphthalenetetracarboxylic acid diimide derivative are connected to each other, transmitted electrons are transferred through delivery between the connected molecules. Hence, in order to increase electron transferring ability, the naphthalenetetracarboxylic acid diimide derivative molecules should be evenly dispersed throughout an organic solvent and be well connected to each other. If $R_1$ or $R_2$ is an alkyl group having more than 20 carbon atoms, the binding between the naphthalenetetracarboxylic acid diimide derivative molecules is not easily achieved and thus, the electron transportation becomes difficult. Accordingly, $C_1$-$C_{20}$ alkyl group is preferred, and a $C_1$-$C_{12}$ alkyl group is more preferred. Examples of suitable alkyl groups include methyl, ethyl, n-propyl, isopropyl, n-butyl, isobutyl, sec-butyl, t-butyl, pentyl, hexyl, 1,2-dimethylpropyl, and 2-ethylhexyl, but are not limited to these examples.

If $R_1$ or $R_2$ is an alkoxy group, the alkoxy group may be a straight or branched $C_1$-$C_{20}$ alkoxy group. If $R_1$ or $R_2$ is an alkoxy group having more than 20 carbon atoms, the binding between the naphthalenetetracarboxylic acid diimide derivative molecules is not easily achieved and the dispersion in the organic solvent is not even, which make the electron transportation difficult. Accordingly, a $C_1$-$C_{20}$ alkoxy group is preferred. Examples of suitable alkoxy groups include methoxy, ethoxy, propoxy, butoxy, and pentyloxy, but are not limited to these examples.

If $R_1$ or $R_2$ is an aryl group, the aryl group may be a substituted or non-substituted $C_6$-$C_{30}$ aryl group. If the aryl group has more than 30 carbon atoms, the naphthalenetetracarboxylic acid diimide derivatives become a huge molecule. Thus, for the same reason described above for the alkyl group, and alkoxy group, the electron transportation becomes difficult. Accordingly, the number of carbon atoms of the aryl group is preferably 6 to 30. Examples of suitable aryl groups include phenyl, tolyl, xylyl, biphenyl, o-terphenyl, naphthyl, anthryl, and phenanthryl, but are not limited to these examples.

If $R_1$ or $R_2$ is an aralkyl group, the aralkyl group may be a $C_7$-$C_{30}$ aralkyl group. If the number of carbon atoms of the alkyl group is more than 30, the naphthalenetetracarboxylic acid diimide derivative become a huge molecule. Thus, for the same reason described above for the alkyl group, alkoxy group and aryl group, the electron transportation becomes difficult. Accordingly, the number of carbon atoms of the aralkyl is preferably 7 to 30. The term "aralkyl group" used in the present invention refers collectively to complex groups having a formula of $Ar(CH_2)_n$—, which are formed by substitution of aromatic hydrocarbon group (aryl group), such as phenyl, and tolyl, at a carbon atom of an alkyl group, and is an abbreviation for arylalkyl group. The examples of suitable aralkyl groups include benzyl ($C_6H_5CH_2$—), and phenethyl($C_6H_5CH_2CH_2$—), but are not limited to these examples.

The alkyl group, the alkoxy group and the aralkyl group may independently have a substituent of an alkyl group such as methyl, ethyl, n-propyl, isopropyl, n-butyl, isobutyl, sec-butyl, t-butyl, pentyl, hexyl, 1,2-dimethyl-propyl and 2-ethyl-hexyl; an aryl group such as phenyl, tolyl, xylyl, biphenyl, 0-terphenyl, naphthyl, anthryl, and phenanthryl; a halogen atom such as fluorine, chlorine, bromine and iodine; or an alkoxy group such as or methoxy, ethoxy, propoxy, butoxy and pentoxy, but the usable substituent is not limited to these examples.

The aryl group may have a substituent of an alkyl group such as methyl, ethyl, n-propyl, isopropyl, n-butyl, isobutyl, sec-butyl, t-butyl, pentyl, hexyl, 1,2-dimethyl-propyl and 2-ethyl-hexyl; an halogen atom such as fluorine, chlorine, bromine and iodine; a nitro group; or an alkoxy group such as methoxy, ethoxy, propoxy, butoxy and pentoxy, but the usable substituent is not limited to these examples.

Examples of the naphthalenetetracarboxylic acid diimide derivatives according to one embodiment of the present invention as described above are as follows, but are not limited these examples.

[Formula 5]

-continued

[Formula 6]

[Formula 7]

[Formula 8]

[Formula 9]

[Formula 10]

[Formula 11]

[Formula 12]

-continued

[Formula 13]

[Formula 14]

[Formula 15]

[Formula 16]

[Formula 17]

[Formula 18]

[Formula 19]

[Formula 20]

[Formula 21]

[Formula 22]

[Formula 23]

To synthesize the naphthalenetetracarboxylic acid diimide derivative of the Formula 3, a substituted or non-substituted amino pyridine is reacted with naphthalenetetracarboxylic dianhydride.

A representative reaction scheme for synthesis of the naphthalenetetracarboxylic acid diimide derivative according to an embodiment of the present invention is shown as follows.

Reaction Scheme 1

In the Reaction Scheme 1, if $R_1$ is hydrogen, the product is a naphthalenetetracarboxylic acid diimide derivative of the Formula 5.

Figure 1:
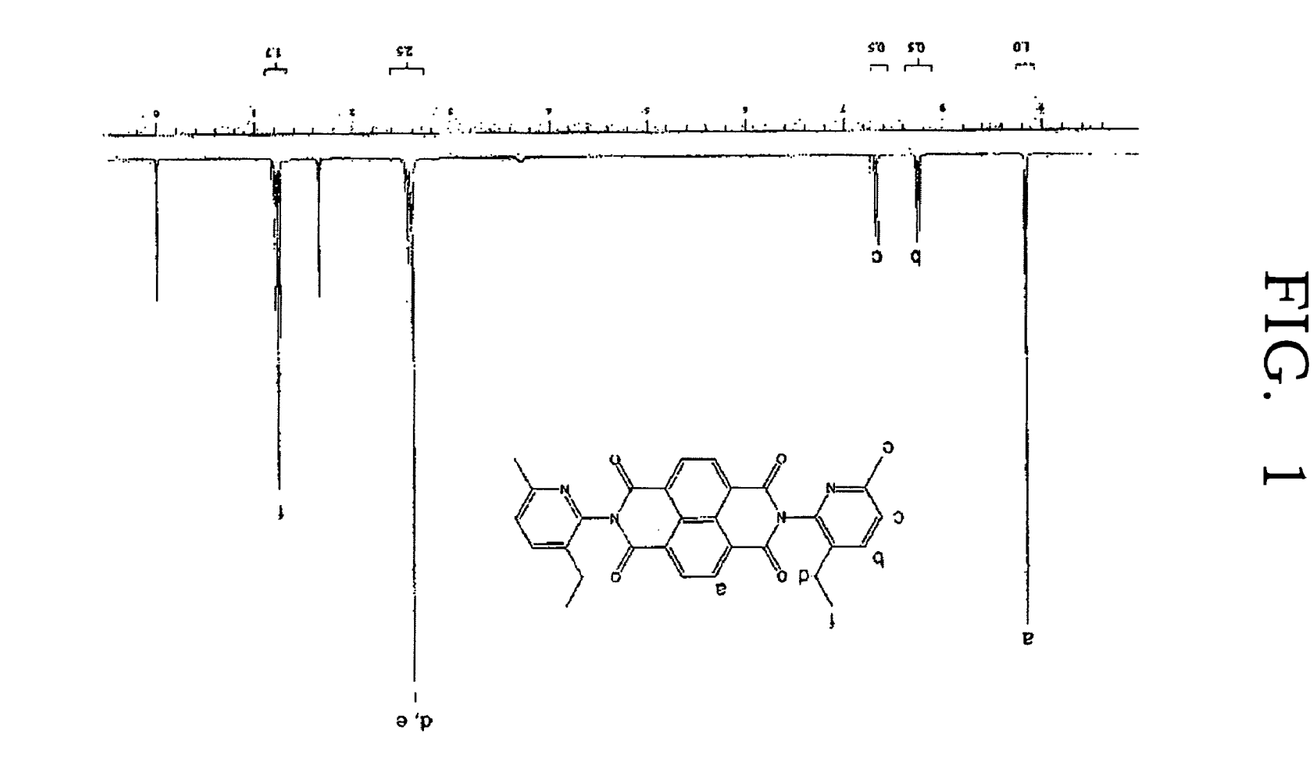
FIG. 1 is a FT-NMR spectrum of a naphthalenetetracarboxylic acid diimide derivative according to an example of the present invention.

A compound of the Formula 5 is synthesized and measured for its NMR and IR spectrums. FIG. 1 illustrates an NMR spectrum of the compound of the Formula 5 dissolved in $CDCl_3$. By this spectrum, functional groups of the compound can be identified.

Figure 2:
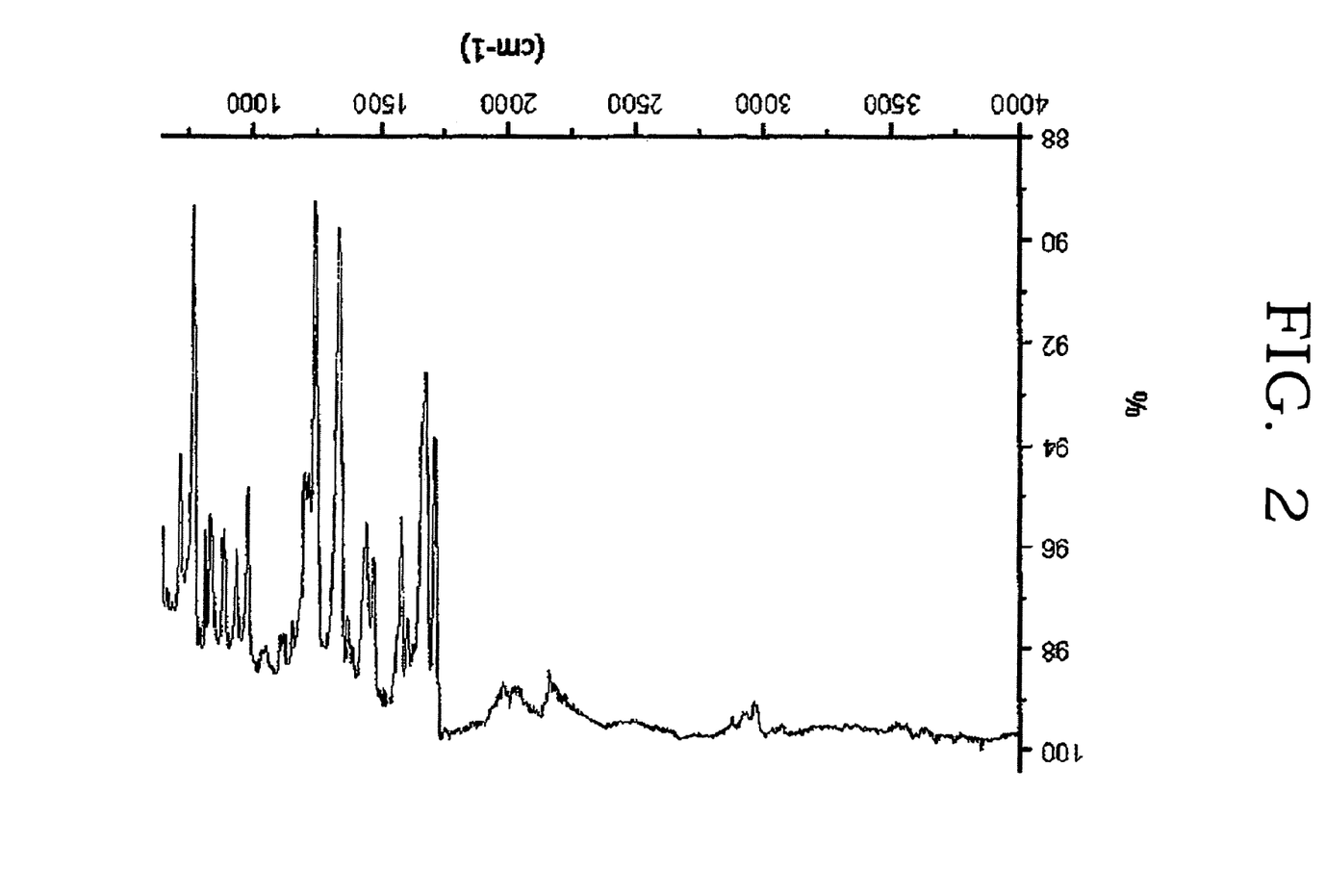
FIG. 2 is a FT-IR spectrum of the naphthalenetetracarboxylic acid diimide derivative of FIG. 1.

FIG. 2 illustrates an IR spectrum of the compound of Formula 5 measured by an infrared spectrophotometer. The vertical axis represents % transmittance and the horizontal axis represents wave number in $cm^{-1}$ unit. By this IR spectrum, functional groups of the compound of Formula 5 can be identified.

The naphthalenetetracarboxylic acid diimide derivatives of Formula 5 through Formula 23 can be obtained by reacting a substituted amino pyridine with naphthalenetetracarboxylic dianhydride, as shown in the Reaction Scheme 1.

The electrophotographic photoconductive material according to the embodiment of the present invention is described below.

Figure 3:
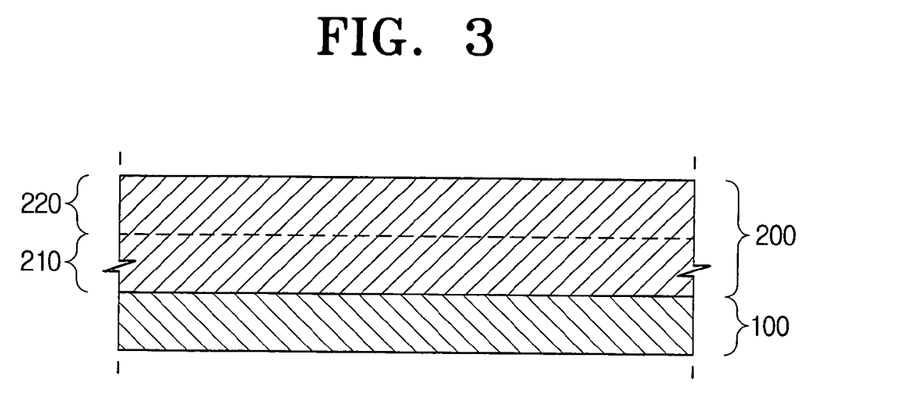
FIG. 3 is a schematic view illustrating a cross-section of the electrophotographic photoconductive material according to an embodiment of the present invention.

FIG. 3 illustrates the electrophotographic photoconductive material according to an embodiment of the present invention. The electrophotographic photoconductive material includes a substrate 100 and a photoconductive layer 200 formed on the substrate 100. The photoconductive layer 200 may be a single-layer type or multi-layer type structure. The single-layer type structure is formed in a single layer and performs without division of a charge generating layer and a charge transferring layer, while the multi-layer type structure is divided into a charge transferring layer 210 and a charge generating layer 220 which have their own discrete role. In FIG. 3, solid lines represent the single-layer type electrophotographic photoconductive material which includes a substrate 100 and a photoconductive layer 200. Dotted lines in the photoconductive layer 200 show the multi-layer type photoconductive layer 200 including a charge generating layer 210 and a charge transferring layer 220, which shows a multi-layer structure electrophotographic photoconductive material.

The substrate should be made of an electrically conductive material. Examples of materials which can be used as the substrate include metals such as aluminum, copper, tin, platinum, gold, silver, vanadium, molybdenum, chrome, cadmium, titanium, nickel, indium, stainless steel or brass, plastics on which the foregoing metals are deposited or laminated, and glass coated with aluminum iodide, tin oxide or indium oxide. Particularly, an aluminum substrate is preferred. The substrate 100 of the electrophotographic photoconductive material is produced in the form of a drum or belt.

The photoconductive layer has a charge generating material and a charge transferring material. The charge generating material may be largely classified into an inorganic charge generating material and an organic charge generating material. The inorganic charge generating material may include zinc oxide, lead oxide and selenium. The organic charge generating material may include various pigment materials including phthalocyanine type pigments, organometals and various soluble organic compounds including polymeric organic charge generating materials. The inorganic charge generating material requires high production cost and may induce environmental pollution. It is preferable to use the organic charge generating material.

Examples of the organic charge generating material include azo pigments, disazo pigments, anthanthrone pigments, phthalocyanine pigments, indigo pigments, threne pigments, toluidine pigments, pyrazoline pigments, phenylene pigments, and quinacridone pigments, which may be used alone or as a mixture of two or more of the pigments. Particularly, phthalocyanine pigments are preferred, which have excellent sensitivity to laser rays and are chemically and physically stable.

Examples of the phthalocyanine pigments include nonmetal phthalocyanine, aluminum phthalocyanine, vanadium phthalocyanine, cadmium phthalocyanine, antimony phthalocyanine, chrome phthalocyanine, copper 4-phthalocyanine, germanium phthalocyanine, zinc phthalocyanine, chloroaluminum phthalocyanine, oxotitanyl phthalocyanine, chloroindium phthalocyanine, chlorogalium phthalocyanine, magnesium phthalocyanine, dialkyl phthalocyanine, tetramethyl phthalocyanine, and tetraphenyl phthalocyanine, but are not limited to these examples.

The charge transferring material contained in photoconductive layer may be largely classified into a hole transferring material and the electron transferring material. The charge transferring material which is used in the present invention is the electron transferring material including the naphthalenetetracarboxylic acid diimide derivatives of the Formula 4.

The charge transferring material may further include a hole transferring material along with the electron transferring material. Examples of the hole transferring material may include poly-N-vinylcarbazole, phenanthrene, N-ethylcarbazole, 2,5-diphenyl-1,3,4-oxadiazole, 2,5-bis-(4-diethylaminophenyl)-1,3,4-oxadiazole, bis-diethylaminophenyl-1, 3,6-oxadiazole, 4,4'-bis(diethylamino)-2,2'-dimethyltriphenylmethane, 2,4,5-triaminophenylimidazole, 2,5-bis(4-diethylaminophenyl)-1,3,4-triazole, 1-phenyl-3-(4-diethylaminostyryl)-5-(4-diethylaminophenyl)-2-pyrazoline, tetra(m-methylphenyl)methaphenylenediamine, N,N, N',N'-tetraphenylbenzidine derivatives, and N,N'-diphenyl-N,N'-disilylbenzidine, but are not limited to these examples.

The charge generating material and the charge transferring material contained in the photoconductive layer are dispersed in the binder resin. Examples of the binder resin include styrene-butadiene copolymers; polyvinyl toluene-styrene copolymers; silicone resins, styrene alkyd resins, silicone-alkyd resins; soya-alkyd resins; poly(vinyl chloride); poly(vinylidene chloride); vinylidene chloride-acrylonitrile copolymers; poly(vinylacetate); vinyl acetate-vinylchloride copolymers; poly(vinylacetal) such as poly (vinylbutyral); polyacrylic- and methacrylic ester such as poly(methylmethacrylate), poly(n-butylmethacrylate) and poly(isobutylmethacrylate); polystyrene, nitrated polystyrene; polymethylstyrene; isobutylene polymers; polyester such as poly[4,4'-(2-norbornylidene)bisphenylene azelate-co-terephthalate (60/40)] and poly[ethylene-co-alkylene-bis (alkylene-oxyaryl)-phenylenedicarboxylate]; phenol-formaldehyde resins; ketone resins; polyamides; polycarbonates; polythiocarbonates; poly[ethylene-co-isopropylidene-2,2-bis(ethyleneoxyphenylene)terephthalate]; copolymers of vinylhaloarylate and vinyl acetate such as poly(vinyl-m-bromobenzoate-co-vinyl acetate); polyolefin chloride such as polyethylene chloride; and equivalents thereof. Particularly, polyester and polycarbonate resins are preferably used.

Preferably, the electrophotographic photoconductive material according to the embodiment of the present invention contains the electron transferring material of the Formula 3 in a ratio of 20 wt % to 40 wt % based on the total weight of the solid components. If the content of the electron transferring material is less than 20 wt %, the electron transferring ability of the electron transferring material is deteriorated, while if the content exceeds 40 wt %, the solubility of the electron transferring material in a solvent is lowered or the compatibility with a binder resin is deteriorated.

The photoconductive layer comprising the electron transferring material of the Formula 3 may be of a single layer structure or a multi-layer structure.

The electrophotographic photoconductive material may further include the electron acceptor in combination with the electron transferring material. Examples of usable electron acceptors include benzoquinone compounds such as p-benzoquinone and 2,6-t-butylbenzoquinone; naphthoquinone compounds such as 1,4-naphthoquinone, 2-t-butyl-3-benzoyl-1,4-naphthoquinone and 2-phenyl-3-benzoyl-1,4-naphthoquinone; and diphenoquinone compounds such as 3,5-dimethyl-3'5'-di-t-butyldiphenoquinone, 3,5-dimethoxy-3', 5'-di-t-butyldiphenoquinone, 3,3'-dimethyl-5,5'-di-t-butyldiphenoquinone, 3,5'-dimethyl-3',5-di-t-butyldiphenoquinone, 3,5,3',5'-tetramethyldiphenoquinone, 2,6,2',6'-tetra-t-butyldiphenoquinone, 3,5,3',5'-tetraphenyldiphenoquinone and 3,5,3',5'-tetraacyclohexyldiphenoquinone, but are not limited to these examples.

The lamination of the photoconductive layer on the substrate is performed by preparing a coating solution including the charge generating material and the charge transferring material, as described above, and applying the coating solution on the substrate. The coating solution is prepared using an organic solvent. Examples of organic solvents include alcohols such as methanol, ethanol, isopropanol and butanol; aliphatic hydrocarbon compounds such as n-hexane, octane and cyclohexane; aromatic hydrocarbon compounds such as benzene, toluene, and xylene; halogenated hydrocarbon compounds such as dichloromethane, dichloroethane, carbon tetrachloride and chlorobenzene; ethers such as dimethyl ether, diethyl ether, tetrahydrofuran, ethylene glycol dimethyl ether and diethylene glycol dimethyl ether; ketone compounds such as acetone, methyl ethyl ketone and cyclohexane; ester compounds such as ethyl acetate and methyl acetate; and dimethylformamide, and dimethyl sulfoxide. These solvents may be used alone or in combination of two or more of the solvents.

When a substituted pyridine is introduced to an imide structure of the naphthalenetetracarboxylic acid diimide derivative, the molecular structures of the naphthalenetetracarboxylic acid diimide derivative do not align in a single plane due to the steric hindrance. That is, the molecules do not form an overlapping structure and thus, do not crystallize. However, though the crystallization between molecules is difficult, the solubility of the naphthalenetetracarboxylic acid diimide derivative in the organic solvent may increase and the compatibility to a binder resin may be improved.

In the electrophotographic image forming apparatus, nitrogen oxides (NOx) which are generated during corona charging, shortens the life span of the electrophotographic photoconductive material. However, pyridine may serve as an acid acceptor and thus, it is possible to inhibit the effects of the NOx and increase the life span of the electrophotographic photoconductive material by using naphthalenetetracarboxylic acid diimide derivatives that include a pyridine structure to effectively remove the nitrogen oxides.

According to one embodiment of the present invention, the naphthalenetetracarboxylic acid diimide derivatives having the pyridine structure have increased solubility in organic solvents and improved compatibility with binder resins. Also, the nitrogen oxides are effectively removed to prevent reduction of the life span of the electrophotographic photoconductive material.

According to the embodiment of the present invention, the electrophotographic photoconductive material may further include a protective layer between the substrate and the photoconductive layer to improve adhesion between the substrate and the photoconductive layer and to inhibit the immigration of the hole from the substrate to the photoconductive layer, or include a protective layer on the photoconductive layer to protect the photoconductive layer from abrasion during cleaning.

Examples according to the present invention will be explained.

EXAMPLES

Synthesis of Naphthalenetetracarboxylic Acid Diimide Derivatives

Example 1

Reference is made to the Reaction Scheme 1.

10.72 g (0.04 mol) of naphthalene-1,4,5,8-tetracarboxylic acid dianhydride was stirred with 100 ml of dimethylformamide (DMF) at room temperature. A mixture of 11.44 g (0.084 mol) of 2-amino-3-ethyl-6-methylpyridine and 20 ml of DMF was slowly added and stirred for 1 hour at room temperature.

Next, the reaction was refluxed for 3 hours by elevating the temperature, followed by cooling to room temperature. 60 ml of methanol was added to the cooled solution to form precipitates, followed by filtration.

The filtered solids were recrystalized from a solvent mixture of chloroform and ethanol. The recrystallized product was dried in vacuo to obtain 20.0 g of light orange crystals. It was confirmed that the resulting solid has a structure of the Formula 5. The yield was 90%.

Preparation of Electrophotographic Photoconductive Material

Example 2

The parts by weight of each ingredient are based on 100 parts by weight of the total solids content contained in the electrophotographic photoconductive material.

| | |
|---|---|
| Electron transferring material of the Formula 5: | 4.5 parts by weight |
| χ-type $H_2Pc$ of the Formula 24: | 0.9 parts by weight |
| Hole transferring material of the Formula 25 | 9 parts by weight |
| Binder resin of the Formula 26: | 15.9 parts by weight |
| Methylene chloride: | 84 parts by weight |
| 1,1,2-trichloroethane: | 36 parts by weight |

The ingredients in the above weight ratio were sandmilled for 2 hours and dispersed by ultrasonic agitation. The dispersion was coated on an anodized aluminum drum with a thickness of the anodized layer of 5 μm by ring coating and dried at 110° C. for 1 hour to prepare the electrophotographic photoconductive material having a thickness of about 12 to 13 μm.

[Formula 24]

[Formula 25]

[Formula 26]

Example 3

The parts by weight of each ingredient is based on 100 parts by weight of the total solids content contained in the electrophotographic photoconductive material.

| | |
|---|---|
| Electron transferring material of the Formula 5: | 4.05 parts by weight |
| χ-type H$_2$Pc of the Formula 24: | 0.9 parts by weight |
| Hole transferring material of the Formula 25: | 9 parts by weight |
| Binder resin of the Formula 26: | 15.9 parts by weight |
| Methylene chloride: | 84 parts by weight |
| 1,1,2-trichloroethane: | 36 parts by weight |
| Electron acceptor of the following Formula 27: | 0.45 parts by weight |

The ingredients in the above weight ratio were sandmilled for 2 hours and dispersed by ultrasonic agitation. Next, the dispersion was coated on an anodized aluminum drum with a thickness of the anodized layer of 5 μm by ring coating and dried at 110° C. for 1 hour to prepare the electrophotographic photoconductive material having a thickness of about 12 to 13 μm.

[Formula 27]

Comparative Example 1

The parts by weight of each ingredient are based on 100 parts by weight of the total solids content contained in the electrophotographic photoconductive material.

| | |
|---|---|
| Electron transferring material of the Formula 28: | 4.5 parts by weight |
| χ-type H$_2$Pc of the Formula 24: | 0.9 parts by weight |
| Hole transferring material of the Formula 25: | 9 parts by weight |
| Binder resin of the Formula 26: | 15.9 parts by weight |
| Methylene chloride: | 84 parts by weight |
| 1,1,2-trichloroethane: | 36 parts by weight |

The ingredients in the above weight ratio were sandmilled for 2 hours and dispersed by ultrasonic agitation. Next, the dispersion was coated on an anodized aluminum drum with a thickness of the anodized layer of 5 μm by ring coating and dried at 110° C. for 1 hour to prepare the electrophotographic photoconductive material having a thickness of about 12 to 13 μm.

[Formula 28]

Comparative Example 2

The parts by weight of each ingredient are based 100 on parts by weight of the total solids content contained in the electrophotographic photoconductive material.

| | |
|---|---|
| Electron transferring material of the Formula 28: | 4.05 parts by weight |
| χ-type H$_2$Pc of the Formula 24: | 0.9 parts by weight |
| Hole transferring material of the Formula 25: | 9 parts by weight |
| Binder resin of the Formula 26: | 15.9 parts by weight |
| Methylene chloride: | 84 parts by weight |
| 1,1,2-trichloroethane: | 36 parts by weight |
| Electron acceptor of the Formula 27: | 0.45 parts by weight |

The ingredients in the above weight ratio were sandmilled for 2 hours and dispersed by ultrasonic agitation. Next, the dispersion was coated on an anodized aluminum drum with a thickness of the anodized layer of 5 μm by ring coating and dried at 110° C. for 1 hour to prepare the electrophotographic photoconductive material having a thickness of about 12 to 13 μm.

Comparative Example 3

The parts by weight of each ingredient are based 100 on parts by weight of the total solids content contained in the electrophotographic photoconductive material.

| χ-type H₂Pc of the Formula 24: | 0.9 parts by weight |
|---|---|
| Hole transferring material of the Formula 25: | 13.5 parts by weight |
| Binder resin of the Formula 26: | 15.9 parts by weight |
| Methylene chloride: | 84 parts by weight |
| 1,1,2-trichloroethane: | 36 parts by weight |
| Electron transferring material of the Formula 27: | 0.45 parts by weight |

The ingredients in the above weight ratio were sandmilled for 2 hours and dispersed by ultrasonic agitation. Next, the dispersion was coated on an anodized aluminum drum with a thickness of the anodized layer of 5 μm by ring coating and dried at 110° C. for 1 hour to prepare the electrophotographic photoconductive material having a thickness of about 12 to 13 μm.

Comparative Example 4

The parts by weight of each ingredient are based 100 on parts by weight of the total solids content contained in the electrophotographic photoconductive material.

| χ-type H₂Pc of the Formula 24: | 0.9 parts by weight |
|---|---|
| Hole transferring material of the Formula 25: | 13.05 parts by weight |
| Binder resin of the Formula 26: | 15.9 parts by weight |
| Methylene chloride: | 84 parts by weight |
| 1,1,2-trichloroethane: | 36 parts by weight |
| Electron transferring material of the Formula 27: | 0.45 parts by weight |

The ingredients in the above weight ratio were sandmilled for 2 hours and dispersed by ultrasonic agitation. Next, the dispersion was coated on an anodized aluminum drum with a thickness of the anodized layer of 5 μm by ring coating and dried at 110° C. for 1 hour to prepare the electrophotographic photoconductive material having a thickness of about 12 to 13 μm.

Comparative Example 5

The parts by weight of each ingredient are based on 100 parts by weight of the total solids content contained in the electrophotographic photoconductive material.

| Electron transferring material of the Formula 29: | 4.5 parts by weight |
|---|---|
| χ-type H₂Pc of the Formula 24: | 0.9 parts by weight |
| Hole transferring material of the Formula 25: | 9 parts by weight |
| Binder resin of the Formula 26: | 15.9 parts by weight |
| Methylene chloride: | 84 parts by weight |
| 1,1,2-trichloroethane: | 36 parts by weight |

The ingredients in the above weight ratio were sandmilled for 2 hours and dispersed by ultrasonic agitation. Next, the dispersion was coated on an anodized aluminum drum with a thickness of the anodized layer of 5 μm by ring coating and dried at 110° C. for 1 hour to prepare the electrophotographic photoconductive material having a thickness of about 12 to 13 μm.

[Formula 29]

The Formula 29 is a representative example of the Formula 1.

Comparative Example 6

The parts by weight of each ingredient are based on 100 parts by weight of the total solids content contained in the electrophotographic photoconductive material.

| Electron transferring material of the Formula 29: | 4.05 parts by weight |
|---|---|
| χ-type H₂Pc of the Formula 24: | 0.9 parts by weight |
| Hole transferring material of the Formula 25: | 9 parts by weight |
| Binder resin of the Formula 26: | 15.9 parts by weight |
| Methylene chloride: | 84 parts by weight |
| 1,1,2-trichloroethane: | 36 parts by weight |
| Electron acceptor of the following Formula 27: | 0.45 parts by weight |

The ingredients in the above weight ratio were sandmilled for 2 hours and dispersed by ultrasonic agitation. Next, the dispersion was coated on an anodized aluminum drum with a thickness of the anodized layer of 5 μm by ring coating and dried at 110° C. for 1 hour to prepare the electrophotographic photoconductive material having a thickness of about 12 to 13 μm.

{Test}

Potentials of the electrophotographic photoconductive material prepared in Example 2 through Comparative Example 6 are shown in Table 1 below.

TABLE 1

|  | $V_o$ | $V_d$ | $V_o 3000$ | $V_d 3000$ |
|---|---|---|---|---|
| Example 2 | 897 | 87 | 810 | 91 |
| Example 3 | 900 | 88 | 887 | 92 |
| Comp. Example 1 | 825 | 110 | 645 | 132 |
| Comp. Example 2 | 875 | 100 | 809 | 107 |
| Comp. Example 3 | 750 | 150 | 565 | 165 |
| Comp. Example 4 | 723 | 134 | 597 | 140 |
| Comp. Example 5 | 827 | 195 | 644 | 200 |
| Comp. Example 6 | 808 | 155 | 627 | 158 |

Conditions for measuring potentials of respective electrophotographic photoconductive material include Vg=1.0 kV, Iw=300 μA, 0.9 mW LSU power using a scorotron type charger.

In the table, $V_o$ represents an initial charged potential, $V_d$ represents an initial exposure potential, $V_o$ 3000 represents a charged potential after 3000 cycles, and $V_d$ 3000 represents an exposure potential after 3000 cycles.

By comparing the difference ($\Delta V_o$) between $V_o$ and $V_o$ 3000 with the difference ($\Delta V_d$) between $V_d$ and $V_d$ 3000, the potential change of each electrophotographic photoconductive material after several cycles was determined.

The reduction of charged potential and the increase of exposure potential are related to the surface potential of the electrophotographic photoconductive material. The surface potential of the electrophotographic photoconductive material should be maintained at a predetermined level. After the electrophotographic photoconductive material is used several times, the charged potential on the surface is reduced, and thus the image quality is deteriorated. Therefore, it is necessary to maintain the surface potential of the electrophotographic photoconductive material at a predetermined level.

In Example 2, $\Delta V_o$ and $\Delta V_d$ are −87 and 4, respectively, and the difference was not significant. Particularly, in Example 3, $\Delta V_o$ was −13 and the charged potential after 3000 cycles was not significantly changed. That is, after the electrophotographic photoconductive material was used several times, the charged potential was not significantly reduced and the usable time of the electrophotographic photoconductive material was lengthened. The effect was multiplied when the electron acceptor was used. That is, after use for a long period of time, the image quality could be maintained to some degree.

However, in Comp. Example 1 through Comp. Example 6, $\Delta V_o$ and $\Delta V_d$ were large. Particularly, in Comp. Example 5 and Comp. Example 6 which used the electron transferring material disclosed in U.S. Pat. No. 5,468,583, the effects were inferior to those of Example 2 and Example 3.

Therefore, the electrophotographic photoconductive material having the electron transferring material according to the embodiment of the present invention has excellent electron transferring ability, which may prolong the life span of the electrophotographic photoconductive material.

As described above, according to the embodiment of the present invention, it is possible to provide the naphthalenetetracarboxylic acid diimide derivatives having increased solubility in organic solvents and improved compatibility with binder resins. Also, by using the naphthalenetetracarboxylic acid diimide derivatives, it is possible to produce the electrophotographic photoconductive material having excellent electron transferring ability and prolonged usable period, and being capable of producing good quality images after use for a long period of time.

Although the present invention has been illustrated and explained in detail by various embodiments described above, it should be understood that the present invention is not limited thereto, various modifications and changes can be made by those skilled in the art, without departing from the scope and spirit of the invention as disclosed in the accompanying claims and such modifications and changes fall in the scope of the present invention.

What is claimed is:

1. A naphthalenetetracarboxylic acid diimide derivative represented by the following formula:

in which, $R_1$ and $R_2$ are each independently selected from the group consisting of a substituted or non-substituted $C_6$-$C_{30}$ aryl group; and a substituted or non-substituted $C_7$-$C_{30}$ aralkyl group.

2. The naphthalenetetracarboxylic acid diimide derivative according to claim 1, wherein said substituted aralkyl group is substituted with a substituent selected from the group consisting of an alkyl group, an aryl group, a halogen atom and an alkoxy group.

3. The naphthalenetetracarboxylic acid diimide derivative according to claim 1, wherein said substituted aryl group is substituted with a substituent selected from the group consisting of an alkyl group, an alkoxy group, a nitro group and a halogen atom.

4. An electrophotographic photoconductive material comprising a substrate and a photosensitive layer formed on the substrate, wherein said photosensitive layer comprises a charge generating material and a charge transferring material, said charge transferring material being an electron transferring material and wherein said electron transferring material comprises a naphthalenetetracarboxylic acid diimide derivative represented by the following formula:

in which, $R_1$ and $R_2$ are each independently selected from the group consisting of a substituted or non-substituted $C_1$-$C_{20}$ alkyl group; a substituted or non-substituted $C_1$-$C_{20}$ alkoxy group; a substituted or non-substituted $C_6$-$C_{30}$ aryl group; and a substituted or non-substituted $C_7$-$C_{30}$ aralkyl group; and halogen.

5. The electrophotographic photoconductive material according to claim 4, wherein said substituted alkyl group, said substituted alkoxy group and said substituted aralkyl group are independently substituted with a substituent selected from the group consisting of an alkyl group, an aryl group, a halogen atom and an alkoxy group.

6. The electrophotographic photoconductive material according to claim 4, wherein said substituted aryl group is substituted with a substituent selected from the group consisting of an alkyl group, an alkoxy group, a nitro group and a halogen atom.

7. The electrophotographic photoconductive material according to claim 4, wherein said electrophotographic photoconductive material contains said electron transferring material of the above formula in a ratio of 20 wt % to 40 wt % based on the total weight of the solid components.

8. The electrophotographic photoconductive material according to claim 4, wherein said electrophotographic photoconductive material further comprises a hole transferring material.

9. The electrophotographic photoconductive material according to claim 8, wherein said hole transferring material include at least one selected from the group consisting of poly-N-vinylcarbazole, phenanthrene, N-ethylcarbazole, 2,5-diphenyl-1,3,4-oxadiazole, 2,5-bis-(4-diethylaminophenyl)-1,3,4-oxadiazole, bis-didiethylaminophenyl-1,3,6-oxadiazole, 4,4'-bis(diethylamino)-2,2'-dimethyltriphenylmethane, 2,4,5-triaminophenylimidazole, 2,5-bis(4-diethylaminophenyl)-1,3,4-triazole, 1-phenyl-3-(4-diethylaminostyryle)-5-(4-diethylaminophenyl)-2-pyrazoline, tetra(m-methylphenyl)methaphenylenediamine, N,N,N',N'-tetraphenylbenzidine derivatives and N,N'-diphenyl-N,N'-disilylbenzidine.

10. The electrophotographic photoconductive material according to claim 4, wherein said photosensitive layer has a single-layer structure comprising said charge generating material and said naphthalenetetracarboxylic acid diimide derivative together dispersed in said photosensitive layer.

11. The electrophotographic photoconductive material according to claim 4, wherein said photosensitive layer has a multi-layer structure comprising said charge generating material and said naphthalenetetracarboxylic acid diimide derivative dispersed in discrete layers.

12. The electrophotographic photoconductive material according to claim 4, wherein said electrophotographic photoconductive material further comprises an electron acceptor.

13. The electrophotographic photoconductive material according to claim 12, wherein said electron acceptor includes at least one selected from the group consisting of benzoquinone compounds such as p-benzoquinone and 2,6-t-butylbenzoquinone; naphthoquinone compounds such as 1,4-naphthoquinone, 2-t-butyl-3-benzoyl-1,4-naphthoquinone and 2-phenyl-3-benzoyl-1,4-naphthoquinone; and diphenoquinone compounds such as 3,5-dimethyl-3'5'-di-t-butyldiphenoquinone, 3,5-dimethoxy-3',5'-di-t -butyldiphenoquinone, 3,3'-dimethyl-5,5'-di-t-butyldiphenoquinone, 3,5'-dimethyl-3'5-di-t -butyldiphenoquinone, 3,5,3',5'-tetramethyldiphenoquinone, 2,6,2',6'-tetra-t -butyldiphenoquinone, 3,5,3',5'-tetraphenyldiphenoquinone and 3,5,3',5'-tetraacyclohexyldiphenoquinone.

* * * * *